United States Patent
Wilk

(10) Patent No.: US 8,157,725 B1
(45) Date of Patent: Apr. 17, 2012

(54) PORT EXTRACTION KIT FOR TRANS-ORGAN SURGERY

(75) Inventor: Peter J. Wilk, New York, NY (US)

(73) Assignee: Wilk Patent, LLC, New York, NY (US)

( * ) Notice: Subject to any disclaimer, the term of this patent is extended or adjusted under 35 U.S.C. 154(b) by 158 days.

(21) Appl. No.: 12/658,103

(22) Filed: Feb. 1, 2010

Related U.S. Application Data

(62) Division of application No. 11/389,855, filed on Mar. 27, 2006, now Pat. No. 7,785,251.

(60) Provisional application No. 60/674,003, filed on Apr. 22, 2005.

(51) Int. Cl.
*A61B 1/00* (2006.01)

(52) U.S. Cl. ......................... 600/104; 606/140

(58) Field of Classification Search .................. 600/104, 600/105, 114, 159; 606/140; 128/898
See application file for complete search history.

(56) References Cited

U.S. PATENT DOCUMENTS

| | | | |
|---|---|---|---|
| 3,253,594 A | 5/1966 | Matthews et al. | |
| 4,836,204 A | 6/1989 | Landymore et al. | |
| 5,211,624 A | 5/1993 | Cinberg et al. | |
| 5,215,521 A * | 6/1993 | Cochran et al. | 604/22 |
| 5,297,536 A | 3/1994 | Wilk | |
| 5,354,270 A | 10/1994 | Wilk et al. | |
| 5,370,647 A | 12/1994 | Graber et al. | |
| 5,413,571 A | 5/1995 | Katsaros et al. | |
| 5,458,131 A | 10/1995 | Wilk | |
| 5,470,320 A | 11/1995 | Tiefenbrun et al. | |
| 5,480,410 A | 1/1996 | Cuschieri et al. | |
| 5,545,179 A | 8/1996 | Williamson, IV | |
| 5,810,721 A | 9/1998 | Meuller et al. | |
| 5,906,577 A | 5/1999 | Beane et al. | |
| 6,017,305 A | 1/2000 | Bonutti | |
| 6,033,426 A | 3/2000 | Kaji | |
| 6,102,928 A | 8/2000 | Bonutti | |
| 6,245,076 B1 | 6/2001 | Yan | |
| 7,214,185 B1 | 5/2007 | Rosney et al. | |
| 2002/0026094 A1 | 2/2002 | Roth | |
| 2003/0014076 A1 | 1/2003 | Mollenauer et al. | |
| 2006/0212063 A1 | 9/2006 | Wilk | |

* cited by examiner

*Primary Examiner* — Vy Q Bui

(74) *Attorney, Agent, or Firm* — Coleman Sudol Sapone, P.C.; R. Neil Sudol

(57) ABSTRACT

A surgical method for removing a port element disposed in an incision or perforation in a wall of a hollow internal organ in a trans-organ surgical procedure. A distal end portion of a tubular member is inserted into the internal organ through a natural body opening. A capture member is ejected from the distal end portion of the tubular member and receives the port element.

13 Claims, 4 Drawing Sheets

PORT EXTRACTION KIT FOR TRANS-ORGAN SURGERY

CROSS-REFERENCE TO RELATED APPLICATION

This application is a division of application Ser. No. 11/389,855 filed 27 Mar. 2006 and claims the benefit of U.S. Provisional Patent Application No. 60/674,003 filed Apr. 22, 2005.

BACKGROUND OF THE INVENTION

This invention relates to medical procedures carried out without the formation of an incision in a skin surface of the patient.

Such procedures are described in U.S. Pat. Nos. 5,297,536 and 5,458,131.

As described in those patents, a method for use in intra-abdominal surgery comprises the steps of (a) inserting an incising instrument with an elongate shaft through a natural body opening into a natural body cavity of a patient, (b) manipulating the incising instrument from outside the patient to form a perforation in an internal wall of the natural internal body cavity, and (c) inserting a distal end of an elongate surgical instrument through the natural body opening, the natural body cavity and the perforation into an abdominal cavity of the patient upon formation of the perforation. Further steps of the method include (d) inserting a distal end of an endoscope into the abdominal cavity, (e) operating the surgical instrument to perform a surgical operation on an organ in the abdominal cavity, (f) viewing the surgical operation via the endoscope, (g) withdrawing the surgical instrument and the endoscope from the abdominal cavity upon completion of the surgical operation, and (h) closing the perforation.

Visual feedback may be obtained as to position of a distal end of the incising instrument prior to the manipulating thereof to form the perforation. That visual feedback may be obtained via the endoscope or, alternatively, via radiographic or X-ray equipment.

The abdominal cavity may be insufflated prior to the insertion of the distal end of the endoscope into the abdominal cavity. Insufflation may be implemented via a Veress needle inserted through the abdominal wall or through another perforation in the internal wall of the natural body cavity. That other perforation is formed by the Veress needle itself. U.S. Pat. No. 5,209,721 discloses a Veress needle that utilizes ultrasound to detect the presence of an organ along an inner surface of the abdominal wall.

A method in accordance with the disclosures of U.S. Pat. Nos. 5,297,536 and 5,458,131 comprises the steps of (i) inserting an endoscope through a natural body opening into a natural body cavity of a patient, (ii) inserting an endoscopic type incising instrument through the natural body opening into the natural body cavity, (iii) manipulating the incising instrument from outside the patient to form a perforation in an internal wall of the natural internal body cavity, (iv) moving a distal end of the endoscope through the perforation, (v) using the endoscope to visually inspect internal body tissues in an abdominal cavity of the patient, (vi) inserting a distal end of an elongate surgical instrument into the abdominal cavity of the patient, (vii) executing a surgical operation on the internal body tissues by manipulating the surgical instrument from outside the patient, (viii) upon completion of the surgical operation, withdrawing the surgical instrument and the endoscope from the abdominal cavity, (ix) closing the perforation, and (x) withdrawing the endoscope from the natural body cavity.

The surgical procedures of U.S. Pat. Nos. 5,297,536 and 5,458,131 reduce trauma to the individual even more than laparoscopic procedures. Hospital convalescence stays are even shorter. There are some potential problems with the procedures, such as the removal of port elements inserted into the hollow internal organs for purposes of facilitating instrument passage through the organ walls.

The surgical procedures of U.S. Pat. Nos. 5,297,536 and 5,458,131 may be termed "trans-organ" surgical operations inasmuch as they involve the passage of elongate instruments through one organ in order to effectuate surgery on other tissues outside of the organ.

OBJECTS OF THE INVENTION

It is an object of the present invention to provide improvements on the afore-described surgical procedures.

It is another object of the present invention to provide a method for the removal of port elements that are inserted into the hollow internal organs for purposes of facilitating instrument passage through the organ walls.

These and other objects of the present invention will be apparent from the drawings and detailed descriptions herein. While every object of the invention is believed to be attained in at least one embodiment of the invention, there is not necessarily any single embodiment that achieves all of the objects of the invention.

SUMMARY OF THE INVENTION

A surgical method in accordance with the present invention comprises (1) disposing a port element in an incision or perforation formed in a wall of a hollow internal organ that communicates with a natural body opening, (2) subsequently inserting distal end portions of elongate surgical instruments through the natural body opening and an aperture in the port element and concomitantly through the incision or perforation into an internal body cavity, (3) subsequently inserting a distal end portion of a tubular member into the internal organ, (4) thereafter ejecting a capture member from the distal end portion of the tubular member, (5) separating the port element from the organ wall, (6) moving the separated port element into the capture member, and (7) withdrawing the capture member together with the separated port element out of the hollow internal organ through the natural body opening.

The ejecting of the capture member from the distal end portion of the tubular member typically includes expanding the capture member from a collapsed configuration to an expanded configuration.

The capture member may take the form of a cone. In that case, the expanded configuration of the cone has an apex facing the distal end portion of the tubular member and an open base facing away from the distal end portion of the tubular member. The moving of the port element into the capture member includes extending an entrainment tool from the tubular member and through the cone and operating the entrainment tool to entrain the port element and draw the port element into the cone. The entrainment tool may be a forceps, a grasper, or a hook.

Alternatively, the capture member may be a bag or pouch. Then, the moving of the port element into the capture member includes inserting an entrainment tool into the internal organ and manipulating the entrainment tool to entrain the port element and draw the port element into the bag or pouch.

A surgical kit in accordance with the present invention comprises a port element, a tubular member and a capture member. The port element has an aperture and is dispoable in an incision or perforation formed in a wall of a hollow internal organ that communicates with a natural body opening. The tubular member is long enough to insert through the natural body opening into the internal organ. The capture member is ejectable from a distal end of the tubular member for receiving the port element after a separation thereof from the organ wall.

The capture member is preferably stored in a collapsed configuration inside the tubular member and is expandable to an expanded configuration upon ejection from the tubular member.

The capture member may take the form of a cone, the cone in the expanded configuration having an apex proximate the distal end portion of the tubular member and an open base facing away from the distal end portion of the tubular member. The kit may further comprise an entrainment tool extendable from the tubular member and through the cone and operable to entrain the port element and draw the port element into the cone.

Alternatively, the capture member may be a bag or pouch, the kit further comprising an entrainment tool extendable from the tubular member and manipulatable to entrain the port element and draw the port element into the bag or pouch.

The kit may further comprise at least one elongate surgical instrument having a shaft long enough to extend through the natural body opening and the aperture and concomitantly through the incision or perforation into an internal body cavity.

DETAILED DESCRIPTION

Figure 1A:
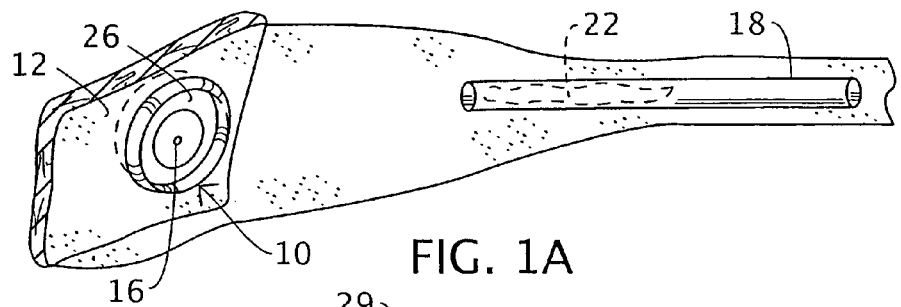
FIGS. 1A-1E are schematic perspective views of a trans-organ port device and an instrument for removing the port device from a patient, showing successive steps using the instrument to extract the port device from a patient's body.

FIG. 1A depicts a port device 10 attached to a wall 12 of a hollow internal organ to facilitate a passage of elongate surgical instruments through the organ and the wall for the performance of a surgical operation on internal body tissues outside of the organ. The organ communicates with a natural body opening such as the mouth, vagina, colon, or urinary bladder. Such procedures are described in U.S. Pat. Nos. 5,297,536 and 5,458,131.

Port element 10 is disposed in an incision or perforation 14 (FIG. 1E) formed in organ wall 12. Distal end portions of elongate surgical instruments are inserted through the natural body opening (not shown) and an aperture 16 in the port element 10 and concomitantly through the incision or perforation 14 into an internal body cavity such as the abdominal cavity. Subsequently, after the termination of the intra-abdominal operation and the withdrawal of the trans-organ surgical instruments from the patient through aperture 16, the hollow internal organ and the natural body opening, a distal end portion of a tubular member 18 is inserted into the internal organ. As indicated in FIG. 1A, tubular member 18 contains a capture member 20 in a collapsed configuration 22.

Figure 1B:
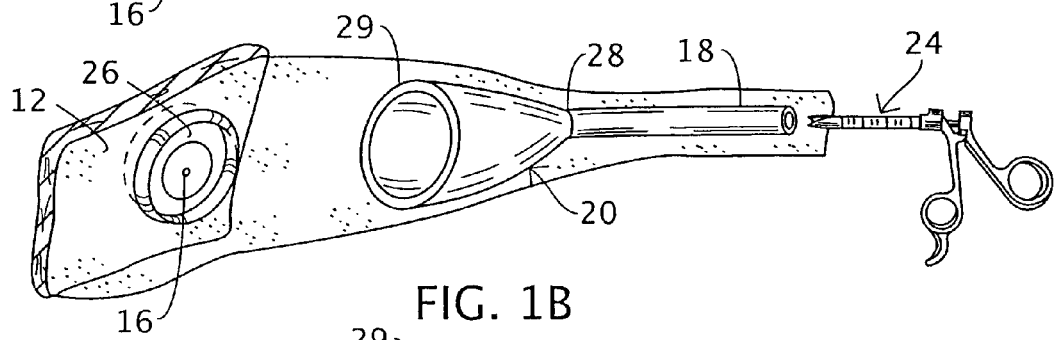

After the insertion of the distal end portion of tubular member 18 into the hollow internal organ through the associated natural body opening, the capture member 20 is ejected from the distal end portion of the tubular member 18. Upon ejection from tubular member 18, capture member 20 automatically expands in response to internal spring forces to assume a conical shape, as shown in FIG. 1B. This capture cone 20 is made at least in part of shape memory material such as Nitinol. Capture cone 20 may incorporate Nitinol ribs and rings (not shown) that give rise to the internal spring forces that cause the opening of the cone.

Figure 1C:
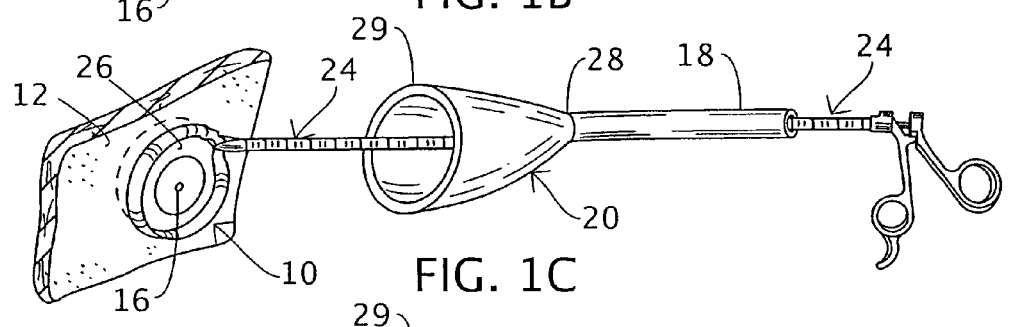

After the ejection and opening of capture cone 20, an entrainment tool 24 such as a forceps, graspers or hook is pushed out of tubular member 18 and through the capture cone 20. The forceps 24 is manipulated form outside the patient to grasp port element 10 and remove it from the organ wall 12. Where port element 10 includes a balloon 26 (see U.S. Pat. Nos. 5,297,536 and 5,458,131), forceps 24 may first puncture the balloon to facilitate separation of the port element 10 from the organ wall 12, as shown in FIG. 1C.

Figure 1D:
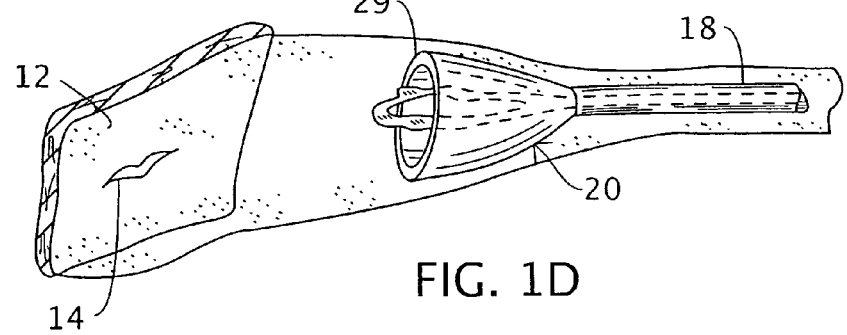
Figure 1E:
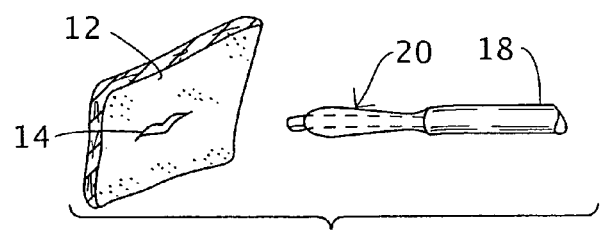

After the port element 10 has been separated from the organ wall 12, forceps 24 is pulled in a proximal direction from outside the patient to draw the port element 10 into the capture cone 20, as depicted in FIG. 1D. Thereafter, the capture cone 20 together with the separated port element 10 is withdrawn from the hollow internal organ through the natural body opening (FIG. 1E). Subsequently, a closure operation may be effectuated on incision 14.

The expanded configuration of the capture cone 20 has an apex 28 proximate the distal end portion of the tubular member 18 and an open base 29 facing away from the distal end portion of the tubular member. Upon the drawing of the separated port element 10 into the capture cone 20, apex 28 of the capture cone may be drawn into the distal end of tubular member 18, for purposes of at least partially closing the cone to aid in the extraction of the cone and its contents from the patient.

Figure 2A:
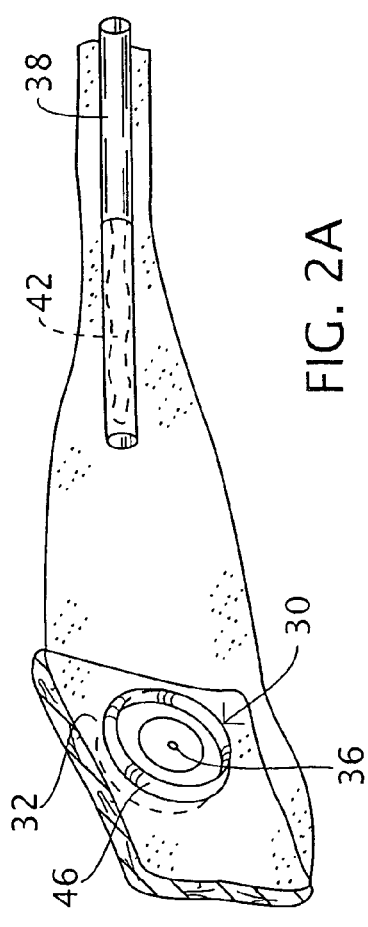
FIGS. 2A-2F are schematic perspective views of a trans-organ port device and another instrument for removing the port device from a patient, showing successive steps using the instrument to extract the port device from a patient's body.

FIG. 2A depicts a port device 30 attached to a wall 32 of a hollow internal organ to facilitate a passage of elongate surgical instruments through the organ and the wall for the performance of a surgical operation on internal body tissues outside of the organ. The organ communicates with a natural body opening such as the mouth, vagina, colon, or urinary bladder. Such procedures are described in U.S. Pat. Nos. 5,297,536 and 5,458,131.

Port element 30 is disposed in an incision or perforation 34 (FIGS. 2D-2F) formed in organ wall 32. Distal end portions of elongate surgical instruments (not shown) are inserted through the natural body opening (not shown) and an aperture 36 in the port element 30 and concomitantly through the incision or perforation 34 into an internal body cavity such as the abdominal cavity. Subsequently, after the termination of the intra-abdominal operation and the withdrawal of the trans-organ surgical instruments from the patient through aperture 36, the hollow internal organ and the natural body opening, a distal end portion of a tubular member 38 is inserted into the internal organ. As indicated in FIG. 2A, tubular member 38 contains a capture member 40 in a collapsed configuration 42.

Figure 2B:
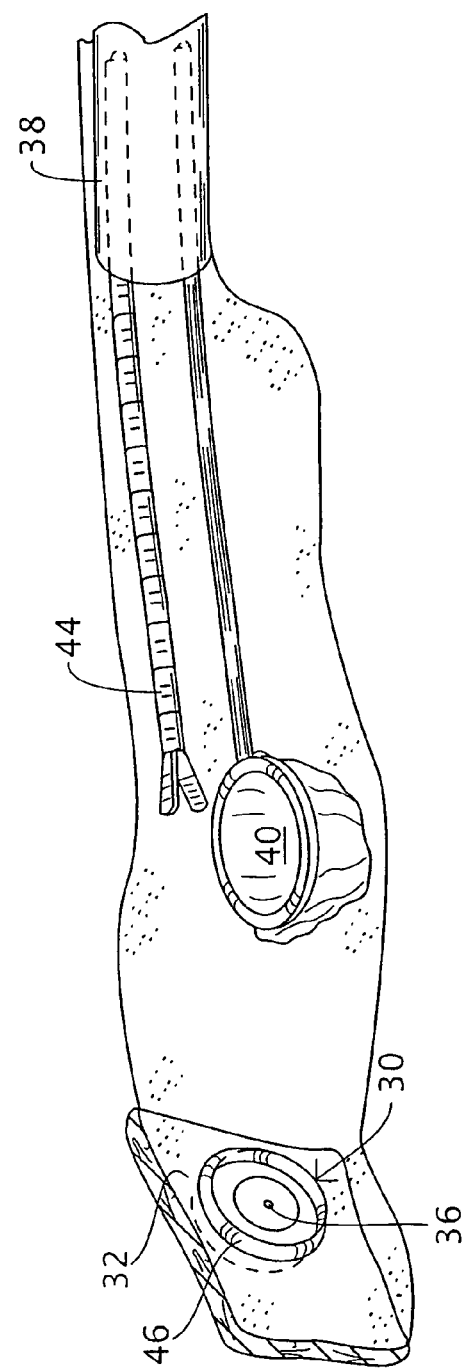

After the insertion of the distal end portion of tubular member 38 into the hollow internal organ through the associated natural body opening, the capture member 40 is ejected from the distal end portion of the tubular member 18. Upon ejection from tubular member 18, capture member 40 automatically expands in response to internal spring forces to assume an expanded shape in the form of a bag or pouch, as shown in FIG. 2B. This capture pouch 40 may made at least in part of shape memory material such as Nitinol. Capture pouch 40 may incorporate Nitinol ribs and rings (not shown) that give rise to the internal spring forces that cause the opening of the cone.

Figure 2C:
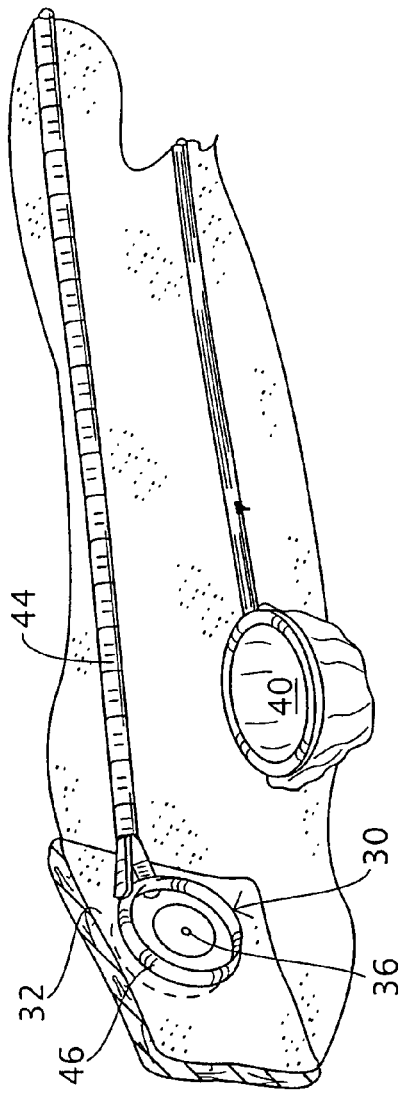

Before or after the ejection and opening of capture cone 40, an entrainment tool 44 such as a forceps, graspers or hook is inserted into the hollow internal organ along the same path as tubular member 38. Entrainment tool 44 may be inserted through tubular member 38 or alongside that tubular member. The entrainment tool 44 is manipulated from outside the patient to grasp port element 30 and remove it from the organ wall 32. Where port element 30 includes a balloon 46, tool 44 may first puncture the balloon to facilitate separation of the port element 30 from the organ wall 32, as shown in FIG. 2C.

Figure 2D:
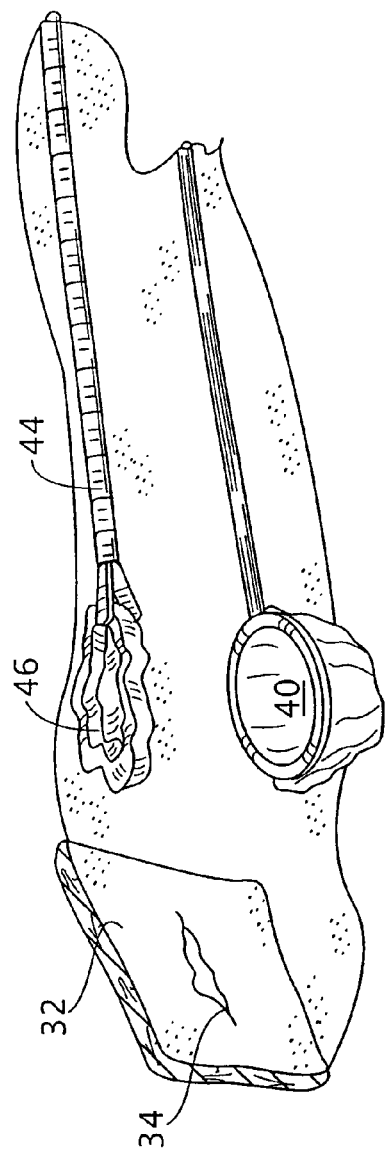
Figure 2E:
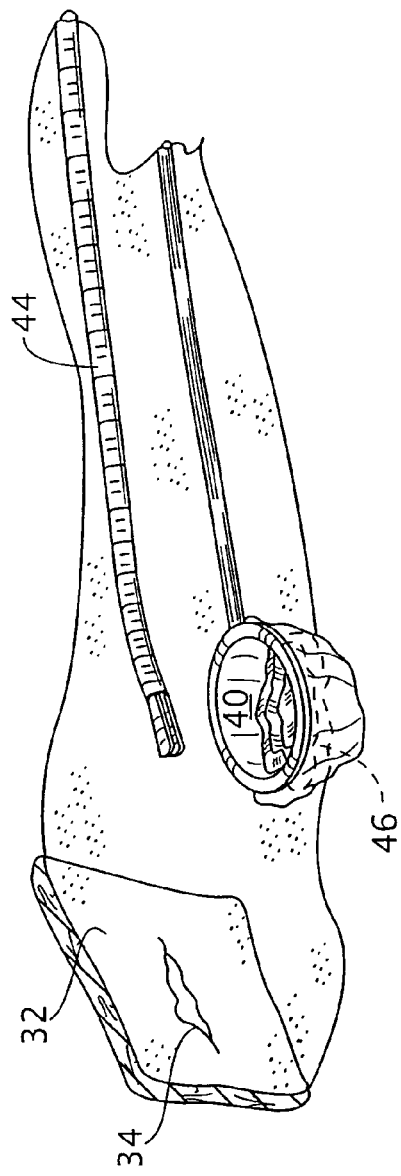
Figure 2F:
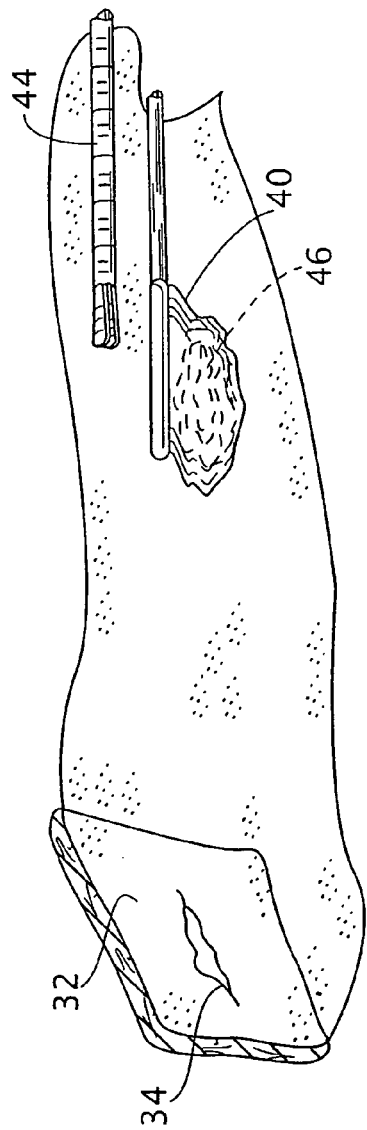

After the port element 30 has been separated from the organ wall 32, tool 44 is manipulated from outside the patient to deposit the port element 30 into the capture pouch 40, as depicted in FIGS. 2D and 2E. Thereafter, the capture pouch 40 carrying the separated port element 30 is withdrawn from the hollow internal organ through the natural body opening (FIG. 2F). Tool 44 is also withdrawn from the patient. Subsequently, a closure operation may be effectuated on incision 34.

The various surgical elements, tools and instruments discussed herein may be distributed together in kits for facilitating delivery, organizing and use in the operating room. Thus, Port element 10 or 30, tubular member 18 or 38, capture member 20 or 40, and entrainment tool 2 or 44, as well as one or more surgical instruments with elongate flexible shafts, may be packaged together.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

The invention claimed is:

1. A surgical kit comprising:
a port element disposable in an incision or perforation formed in a wall of a hollow internal organ that communicates with a natural body opening, said port element having an aperture, said port element including a balloon;
at least one elongate surgical instrument having a shaft long enough to extend through said natural body opening and said aperture and concomitantly through said incision or perforation into an internal body cavity;
a tubular member long enough to insert through said natural body opening into said internal organ;
a capture member ejectable from a distal end of said tubular member for receiving said port element after a separation thereof from the organ wall.

2. The kit defined in claim 1 wherein said capture member is stored in a collapsed configuration inside said tubular member and is expandable to an expanded configuration upon ejection from said tubular member.

3. The kit defined in claim 2 wherein said capture member takes the form of a cone, said cone in said expanded configuration having an apex proximate the distal end portion of said tubular member and an open base facing away from the distal end portion of said tubular member.

4. The kit defined in claim 3, further comprising an entrainment tool extendable from said tubular member and through said cone and operable to entrain said port element and draw said port element into said cone.

5. The kit defined in claim 4 wherein said entrainment tool is taken from the group consisting of a forceps, a graspers, and a hook.

6. The kit defined in claim 2 wherein said capture member is a bag or pouch, further comprising an entrainment tool extendable from said tubular member and manipulatable to entrain said port element and draw said port element into said bag or pouch.

7. The kit defined in claim 6 wherein said entrainment tool is taken from the group consisting of a forceps, a graspers, and a hook.

8. A surgical kit comprising:
a port element dispoable in an incision or perforation formed in a wall of a hollow internal organ that communicates with a natural body opening, said port element having an aperture, said port element including a balloon;
a tubular member long enough to insert through said natural body opening into said internal organ;
a capture member ejectable from a distal end of said tubular member for receiving said port element after a separation thereof from the organ wall.

9. The kit defined in claim 8 wherein said capture member is stored in a collapsed configuration inside said tubular member and is expandable to an expanded configuration upon ejection from said tubular member.

10. The kit defined in claim 9 wherein said capture member takes the form of a cone, said cone in said expanded configuration having an apex proximate the distal end portion of said tubular member and an open base facing away from the distal end portion of said tubular member.

11. The kit defined in claim 10, further comprising an entrainment tool extendable from said tubular member and through said cone and operable to entrain said port element and draw said port element into said cone.

12. The kit defined in claim 9 wherein said capture member is a bag or pouch, further comprising an entrainment tool extendable from said tubular member and manipulatable to entrain said port element and draw said port element into said bag or pouch.

13. The kit defined in claim 8, further comprising at least one elongate surgical instrument having a shaft long enough to extend through said natural body opening and said aperture and concomitantly through said incision or perforation into an internal body cavity.

* * * * *